(12) United States Patent
Polkinghorne et al.

(10) Patent No.: US 7,689,291 B2
(45) Date of Patent: Mar. 30, 2010

(54) LEAD WITH FIBROUS MATRIX COATING AND METHODS RELATED THERETO

(75) Inventors: Jeannette C. Polkinghorne, St. Anthony, MN (US); Xiangchun Jiang, St. Paul, MN (US); Daniel J. Cooke, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 641 days.

(21) Appl. No.: 11/381,018

(22) Filed: May 1, 2006

(65) Prior Publication Data

US 2007/0255378 A1 Nov. 1, 2007

(51) Int. Cl.
*A61N 1/00* (2006.01)

(52) U.S. Cl. ............ 607/115; 977/904; 977/931; 607/36; 607/121

(58) Field of Classification Search .......... 977/904, 977/931; 607/115–132, 36; 600/372–382
See application file for complete search history.

(56) References Cited

U.S. PATENT DOCUMENTS

| | | | |
|---|---|---|---|
| 2,169,250 A | | 8/1939 | Izard et al. |
| 5,571,163 A | * | 11/1996 | Helland ............ 607/123 |
| 5,951,597 A | | 9/1999 | Westlund et al. |
| 6,743,273 B2 | | 6/2004 | Chung et al. |
| 2005/0175657 A1 | | 8/2005 | Hunter et al. |
| 2005/0192665 A1 | | 9/2005 | Spenser et al. |
| 2006/0165952 A1 | * | 7/2006 | Dubrow ............ 428/97 |
| 2007/0067882 A1 | * | 3/2007 | Atanasoska et al. ....... 977/904 |

FOREIGN PATENT DOCUMENTS

| | | |
|---|---|---|
| FR | 2696347 | 4/1994 |
| WO | WO-01/23034 A1 | 4/2001 |
| WO | WO-01/41866 A1 | 6/2001 |
| WO | WO-0141866 A1 | 6/2001 |
| WO | WO-2004/103470 A1 | 12/2004 |
| WO | WO-2004103470 A1 | 12/2004 |
| WO | WO-2007/130900 A2 | 11/2007 |
| WO | WO-2007130900 A3 | 11/2007 |

OTHER PUBLICATIONS

"PCT Application No. PCT/US2007/067757, International Search Report mailed Oct. 26, 2007", 4 pgs.

(Continued)

*Primary Examiner*—Scott M Getzow
(74) *Attorney, Agent, or Firm*—Schwegman, Lundberg & Woessner, P.A.

(57) ABSTRACT

A lead includes a lead body extending from a lead proximal end portion to a lead distal end portion and having an intermediate portion therebetween, one or more tissue sensing/stimulation electrodes disposed along the lead body, one or more terminal connections disposed along the lead proximal end portion. The lead further includes one or more conductors contained within the lead body extending between the tissue sensing/stimulation electrodes and the terminal connections, and a fibrous matrix coating is disposed onto at least a portion of the lead body and/or sensing/stimulation electrodes.

22 Claims, 6 Drawing Sheets

OTHER PUBLICATIONS

"PCT Application No. PCT/US2007/067757, Written Opinion mailed Oct. 26, 2007", 7 pgs.

Lee, J. L., "Polymer Nanoengineering for Biomedical Applications", *Annals of Biomedical Engineering*, 34(1), (2006), 75-88.

Boland, E. D., et al., "Electrospinning collagen and elastin: preliminary vascular tissue engineering", *Front Biosci.*, 9, (May 1, 2004), 1422-32.

Borgaonkar, Harshad, et al., "Conductive Polymeric Coating With Optional Biobeneficial Topcoat for a Medical Lead", U.S. Appl. No. 11/277,858, filed Mar. 28, 2006, 26 pgs.

Grafe, T., et al., "Polymeric Nanofibers and Nanofiber Webs: A New Class of Nonwovens", *INTC 2002: International Nonwovens Technical Conference (Joint INDA—TAPPI Conference)*, (Sep. 24-26, 2002.), 1-13.

Kalluri, R., "Basement membranes: structure, assembly and role in tumour angiogenesis", *Nat Rev Cancer.*, 3(6), (Jun. 2003), 422-33.

Mercier, I., et al., "Interactions of human skin fibroblasts with monomeric or fibrillar collagens induce different organization of the cytoskeleton", *Exp Cell Res.*, 225(2), (Jun. 15, 1996), 245-56.

Schindler, M., et al., "A synthetic nanofibrillar matrix promotes in vivo-like organization and morphogenesis for cells in culture", *Biomaterials*, 26(28), (Oct. 2005), 5624-5631.

Schmeichel, K. L., et al., "Modeling tissue-specific signaling and organ function in three dimensions", *J Cell Sci.*, 116(Pt 12), (Jun. 15, 2003), 2377-88.

Schwarzbauer, J., "Basement membrane: Putting up the barriers", *Current Biology*, 9(7), (Apr. 8, 1999), R242-R244.

Stokes, K. B., et al., "Artificial Electrical Cardiac Stimulation", *Clinical cardiac pacing and defibrillation* / Kenneth A. Ellenbogen, G. Neal Kay, Bruce L. Wilkoff, Chapter 1, Philadephia : W.B. Saunders, (2000), 17-52.

07761564.9, "European Application No. 07761564.9, Office Action mailed Jun. 19, 2009", 7 pgs.

\* cited by examiner

LEAD WITH FIBROUS MATRIX COATING AND METHODS RELATED THERETO

TECHNICAL FIELD

Embodiments relate to fibrous matrix coatings for leads, and specifically, to fibrous matrix coatings for brady, tachy and heart failure leads and associated sensors.

BACKGROUND

Leads represent the electrical link between an implantable medical device (referred to as "IMD"), such as a pacer or defibrillator, and a subject's cardiac or other bodily tissue, which is to be sensed or stimulated. A lead generally includes a lead body that contains one or more electrical conductors extending from a proximal end portion of the lead to an intermediate or distal end portion of the lead. The lead body includes insulating material for covering and electrically insulating the electrical conductors. The proximal end of the lead further includes an electrical connector assembly couplable with the IMD, while the intermediate or distal end portions of the lead include one or more electrodes that may be placed within or near a desired sensing or stimulation site within the body of the subject.

Implantation of leads frequently affects surrounding tissue, and causes inflammation of surrounding tissue. Further, current methods of adhering a lead, such as active or passive fixation, can be inefficient for preventing future dislodgment of the lead. Defibrillating coils also encounter unwanted tissue in-growth which may interfere with their function and the ability to remove the lead.

SUMMARY

Embodiments relate to a lead comprising a lead body extending from a lead proximal end portion to a lead distal end portion and having an intermediate portion therebetween, one or more tissue sensing/stimulation electrodes disposed along the lead body, one or more terminal connections disposed along the lead proximal end portion, one or more conductors contained within the lead body extending between the tissue sensing/stimulation electrodes and the terminal connections and a fibrous matrix coating disposed onto at least a portion of the lead body and/or sensing/stimulation electrodes.

Embodiments also relate to a method of manufacturing a lead, comprising forming a lead and disposing a fibrous matrix coating on all or a portion of the lead.

BRIEF DESCRIPTION OF THE DRAWINGS

In the drawings, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

The following detailed description includes references to the accompanying drawings, which form a part of the detailed description. The drawings show, by way of illustration, specific embodiments in which the present leads and methods may be practiced. These embodiments, which are also referred to herein as "examples," are described in enough detail to enable those skilled in the art to practice the present leads and methods. The embodiments may be combined, other embodiments may be utilized or structural and logical changes may be made without departing from the scope of the present leads and methods. It is also to be understood that the various embodiments of the present leads and methods, although different, are not necessarily mutually exclusive. For example, a particular feature, structure or characteristic described in one embodiment may be included within other embodiments. The following detailed description is, therefore, not to be taken in a limiting sense, and the scope of the present leads and methods are defined by the appended claims and their legal equivalents.

In this document the terms "a" or "an" are used to include one or more than one; the term "or" is used to refer to a nonexclusive or, unless otherwise indicated; and the term "subject" is used synonymously with the term "patient." In addition, it is to be understood that the phraseology or terminology employed herein, and not otherwise defined, is for the purpose of description only and not of limitation.

Furthermore, all publications, patents, and patent documents referred to in this document are incorporated by reference herein in their entirety, as though individually incorporated by reference. In the event of inconsistent usages between this document and those documents so incorporated by reference, the usage in the incorporated references should be considered supplementary to that of this document; for irreconcilable inconsistencies, the usage in this document controls.

Embodiments of the present invention relate to fibrous matrix coatings for medical devices, such as leads. The coating may provide a biocompatible interface for subject tissue to induce a favorable biological response. The coating may reduce the pacing threshold by decreasing fibrotic capsule thickness and improve the healing of injured tissue after implantation. The fibrous matrix coating may also improve tissue-lead interfacial adhesion by promoting tissue in-growth into the matrix. By using material selection, tissue in-growth may be prevented in desired areas, such as into defibrillation electrode coils. In addition, the coating may provide for higher impedance of the lead by selectively coating portions of the lead with an insulating fibrous matrix coating.

The fibrous matrix coating is useful on any medical lead. For example, any medical implantable lead including, but not limited to, cardiac leads, including right-sided and left-sided cardiac leads, positive fixation leads where therapeutic agent is positioned at the fixation mechanism, positive fixation leads where therapeutic agent is positioned at the fixation mechanism that includes an electrode helix, epicardial leads that are sized for implantation through catheter delivery systems, downsized leads where coatings are an option for positioning controlled release therapeutic agent delivery technology, neuro-stimulation leads requiring precise placement of electrode/therapeutic agent releasing components, miniaturized electrodes where coatings can mask to produce high impedance and release agents, and miniaturized leads where a plurality of electrodes can be produced at specific locations by coating/masking.

The coatings also find use on implantable sensing devices, including, but not limited to ion sensors, potassium, calcium and glucose sensors. The term "lead" is used herein in its broadest sense and includes any lead configuration available in the art, including, but not limited to, a stimulation lead, a sensing lead or a combination thereof. Examples of such leads include tachy leads, brady leads and heart failure leads. In one embodiment, the lead is adapted for active fixation. In another embodiment, the lead is adapted for passive fixation. In yet another embodiment, the lead is adapted for bipolar stimulation. In other embodiments, the lead is adapted for defibrillation and/or pacing/sensing. In one embodiment, the lead is tripolar or quadrupolar. In one embodiment, the lead comprises multiple electrodes.

The following text and associated figures begin with a generalized discussion of a lead system (including one or more leads and a medical device), and an environment in which the lead system may be used. Although the following discusses many lead characteristics individually or in specific combinations, any combination of the lead characteristics described herein is within the scope of the present subject matter.

Figure 1:
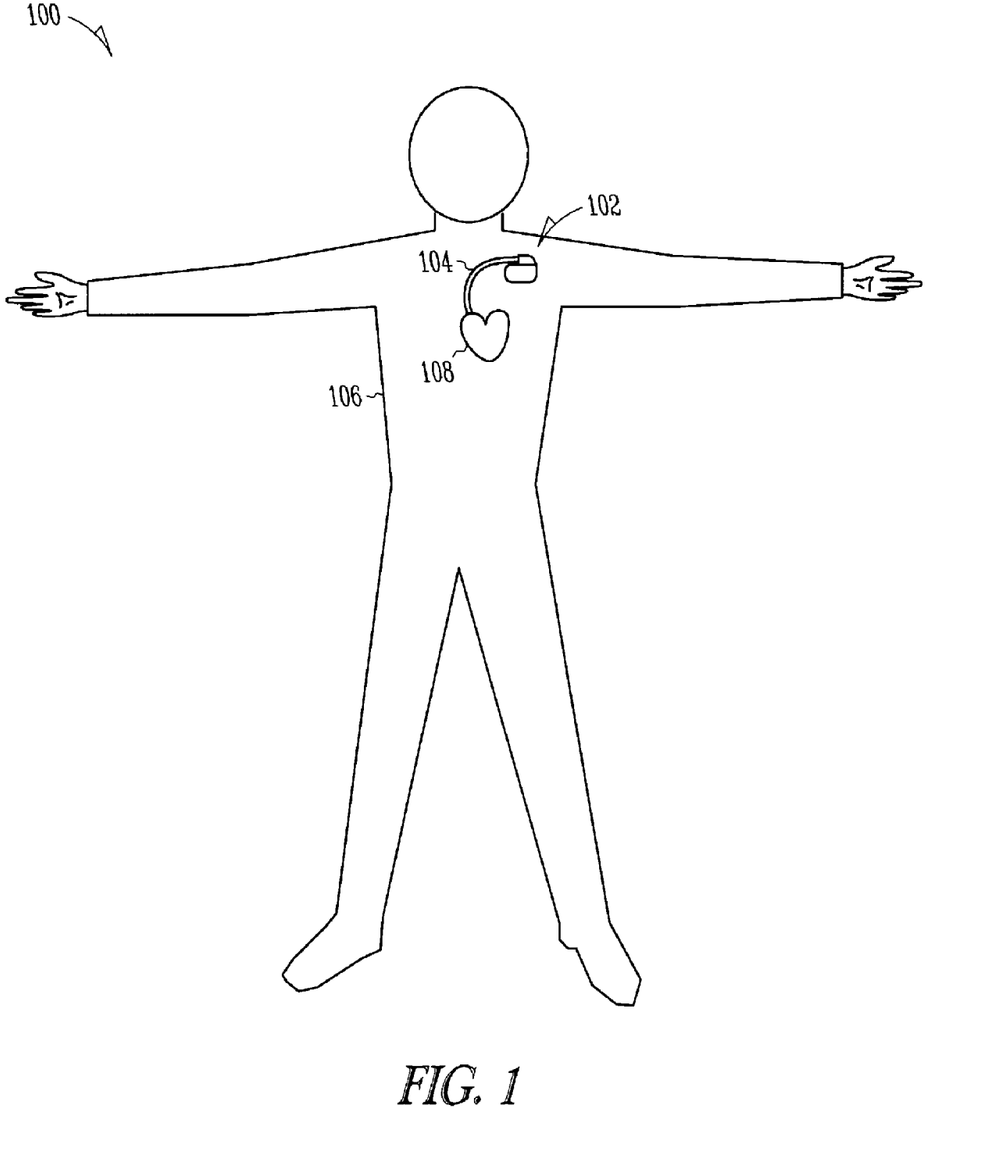
FIG. 1 is a schematic view illustrating an implantable lead system and an environment in which the lead system may be used, according to some embodiments.

Referring to FIG. 1, a lead system 100 and a subject 106 in which lead system 100 may be used is shown, according to some embodiments of the invention. In varying examples, lead system 100 may be used for delivering or receiving electrical pulses or signals to stimulate or sense a heart 108 of a subject 106. As shown in FIG. 1, lead system 100 includes an IMD 102 and an implantable lead 104. IMD 102 generically represents, but is not limited to, cardiac function management (referred to as "CFM") systems such as pacers, cardioverters/defibrillators, pacers/defibrillators, biventricular or other multi-site resynchronization or coordination devices such as cardiac resynchronization therapy (referred to as "CRT") devices, sensing instruments, or drug delivery systems.

Among other things, IMD 102 includes a source of power as well as an electronic circuitry portion. In one example, the electronic circuitry includes microprocessors to provide processing, evaluation, and to determine and deliver electrical shocks or pulses of different energy levels and timing for ventricular defibrillation, cardioversion, or pacing of heart 108 in response to sensed cardiac arrhythmia including fibrillation, tachycardia, or bradycardia. In another example, IMD 102 is a battery-powered device that senses intrinsic signals of heart 108 and generates a series of timed electrical discharges.

Figure 2:
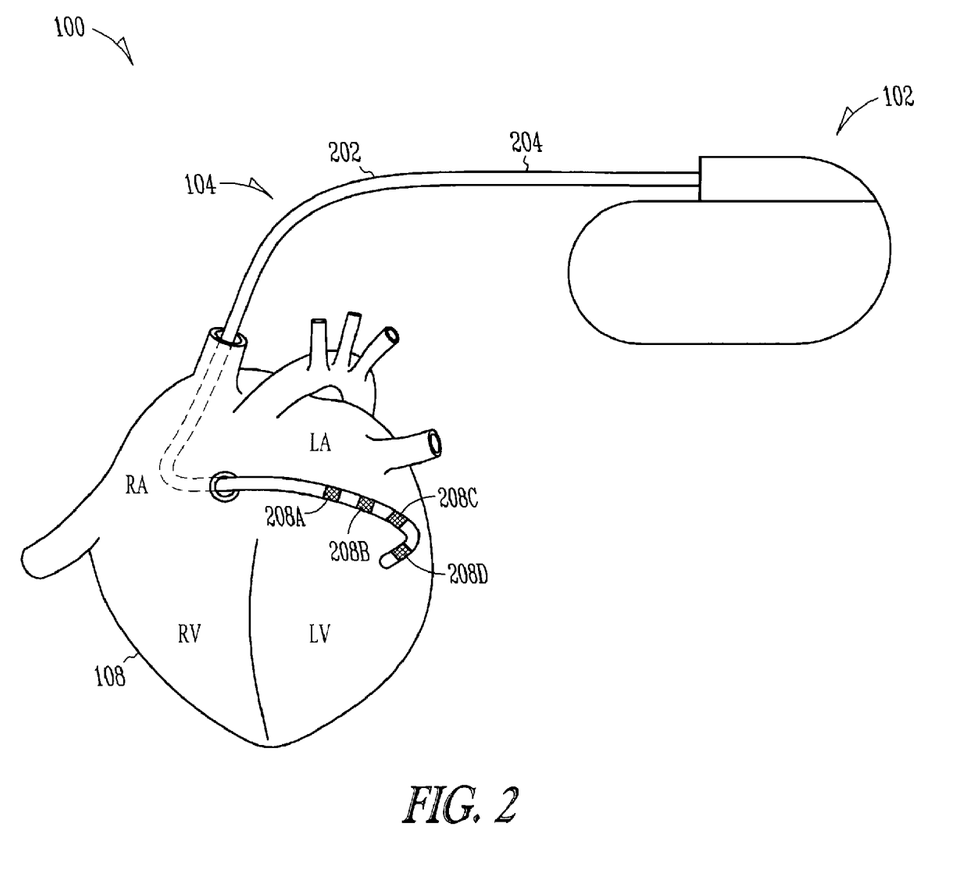
FIG. 2 is a schematic view illustrating an implantable lead system for delivering or receiving signals to or from a heart, according to some embodiments.

Referring to FIG. 2, a schematic view of a lead system 100 including an IMD 102 and an implantable lead 104 is shown, according to some embodiments of the invention. Lead 104 includes a lead body 202 extending from a lead proximal end portion 204, where it is couplable with IMD 102. Lead 104 extends to a lead distal end portion 206, which is positioned within, on, or near a heart 108 when implanted. As shown, lead distal end portion 206 includes at least one electrode 208A, 208B, 208C, 208D that electrically links lead 104 with heart 108. At least one conductor (not shown), electrically couples electrodes 208A, 208B, 208C, 208D with lead proximal end portion 204 and thus, IMD 102. The conductors carry electrical current in the form of pulses or shocks between IMD 102 and electrodes 208A, 208B, 208C, 208D. Lead 104 may be installed using either over-the-wire (referred to as "OTW") or non-OTW techniques, such as stylet driving or catheter delivering.

Figure 3:
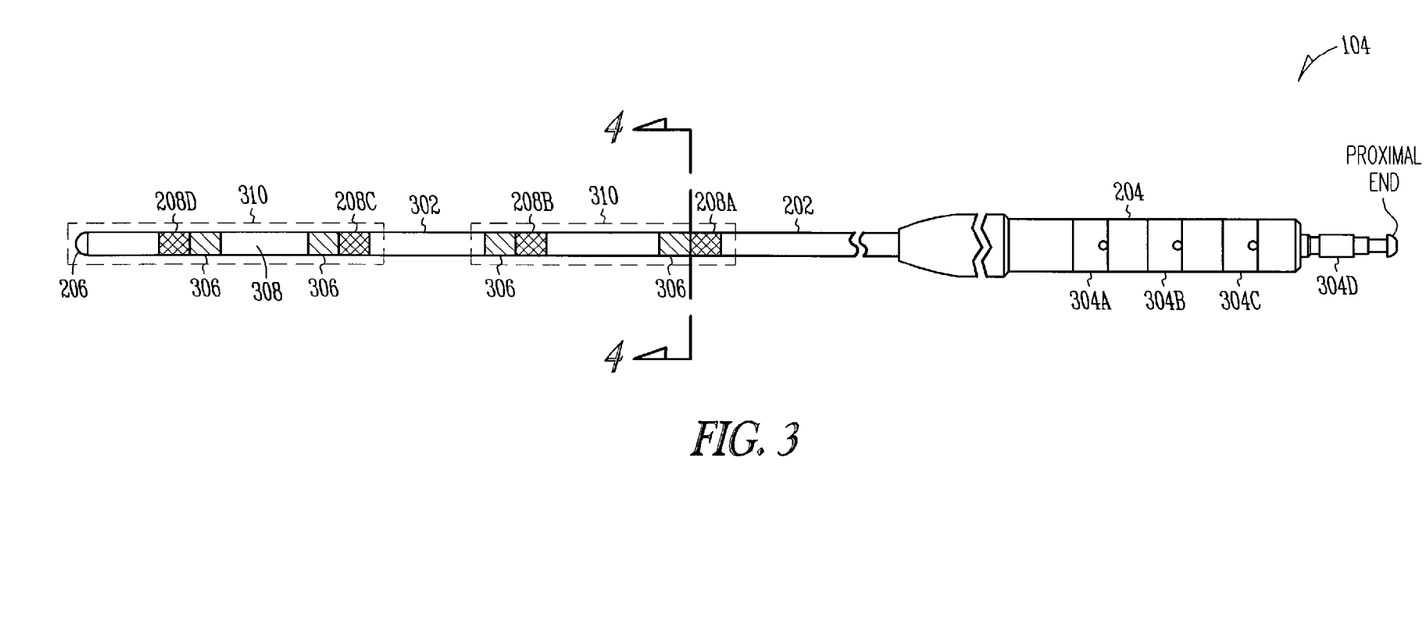
FIG. 3 is a plan view of an implantable lead, according to some embodiments.

Referring to FIG. 3, a plan view of an implantable lead 104 is shown, according to some embodiments of the invention. As shown, lead 104 includes a lead body 202 extending from a lead proximal end portion 204 to a lead distal end portion 206 and having an intermediate portion 302 therebetween. In one example, lead body 202 comprises biocompatible tubing such as medical grade polyurethane. In another example, lead body 202 comprises medical grade silicone rubber. As discussed above in association with FIG. 1, a lead system 100 includes, among other things, lead 104 for electrically coupling an IMD 102 (FIG. 1) to bodily tissue, such as a heart 108 (FIG. 1), which is to be sensed or stimulated by one or more electrodes 208A, 208B, 208C, 208D. It should also be understood that the lead 104 may also include means for sensing other physiological parameters, such as pressure, oxygen saturation, temperature, or the like. As one example, in addition to electrodes 208A, 208B, 208C, 208D, lead 104 may include one or more optional drug collars 306, such as a steroid collar.

As shown in FIG. 3, lead proximal end portion 204 includes one or more terminal connections 304A, 304B, 304C, 304D disposed therealong. Electrodes 208A, 208B, 208C, 208D are each adapted to sense or stimulate heart 108 (FIG. 1) and are electrically coupled to terminal connections 304A, 304B, 304C, 304D via one or more conductors contained within lead body 202, such as in one or more longitudinally extending lumens. Lead proximal end portion 204 and terminal connections 304A, 304B, 304C, 304D disposed therealong are sized and shaped to couple to a multi-pole connector cavity, which may be incorporated into a header (not shown) of IMD 102. It is through the coupling between lead proximal end portion 204 and the multi-pole connector cavity that electrodes 208A, 208B, 208C, 208D are electrically coupled to electronic circuitry of IMD 102. One or more separators 308 may be utilized to electrically isolate the electrodes 208A, 208B, 208C, 208D from one another.

A fibrous matrix coating 310 may cover all or portions of the lead 104, including the one or more electrodes 208A, 208B, 208C, 208D, the one or more drug collars 306, the one or more separators 308, the lead body 202, lead proximal end portion 204, lead distal end portion 206, or intermediate portion 302, for example. The fibrous matrix coating 310 may be formed to mimic the three-dimensional topographical structure of a subject's tissue, such as the extracellular membrane or basement membrane, promoting tissue in-growth and adhesion. The increased adhesion helps to prevent dislodgment of the device.

The coating 310 may be biocompatible, for example. If biocompatible, the coating 310 may attenuate any inflammatory response of the tissue due to implantation of the lead 104. Additionally, by coating portions of the one or more electrodes 208A, 208B, 208C, 208D, a reduced surface area may be exposed which creates a high impedance lead that reduces the battery consumption of the IMD 102.

Figure 4:
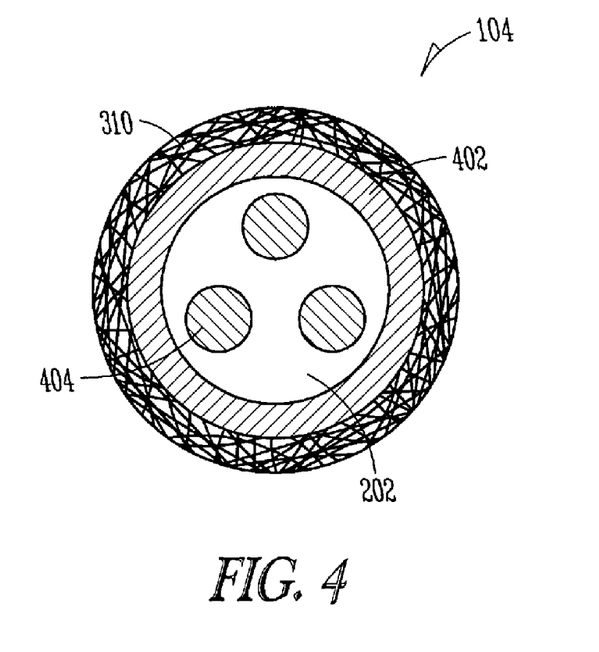
FIG. 4 is a cross-sectional view of an implantable lead taken along line 4-4 of FIG. 3, according to some embodiments.

Referring FIG. 4, an exemplary cross-sectional configuration of a lead body 202 is shown, according to some embodiments of the invention. The lead body 202 may comprise one or more lumens 404 and may be surrounded by an optional modified surface layer 402 and a fibrous matrix coating 310. The optional modified surface layer 402 may comprise a surface of the lead 104 or a separate layer that has been exposed to a surface modification process. Examples of surface modification include plasma etching, chemical etching and electrochemical etching. The surface modification may also include the deposition, sputtering, coating, reactive ion etching or plasma polymerization of a layer of one or more additional functional groups, for example. The modified surface layer 402 may comprise more than one layer and may be positioned underneath or on top of the fibrous matrix coating 310. The modified surface layer 402 may promote increased adhesion or optimization of surface energies of the fibrous matrix coating 310 to the lead 104.

Figure 5:
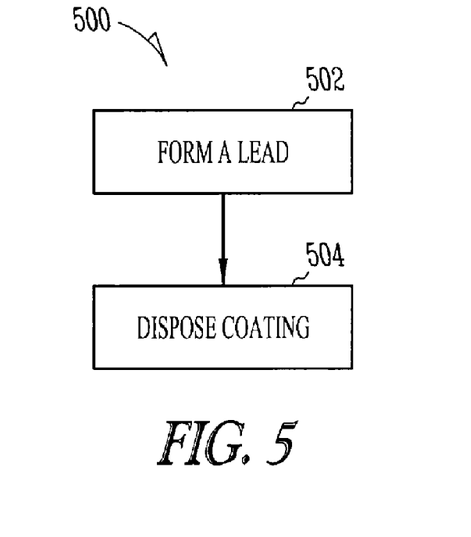
FIG. 5 is a method of manufacturing a lead, according to some embodiments.
Figure 6:
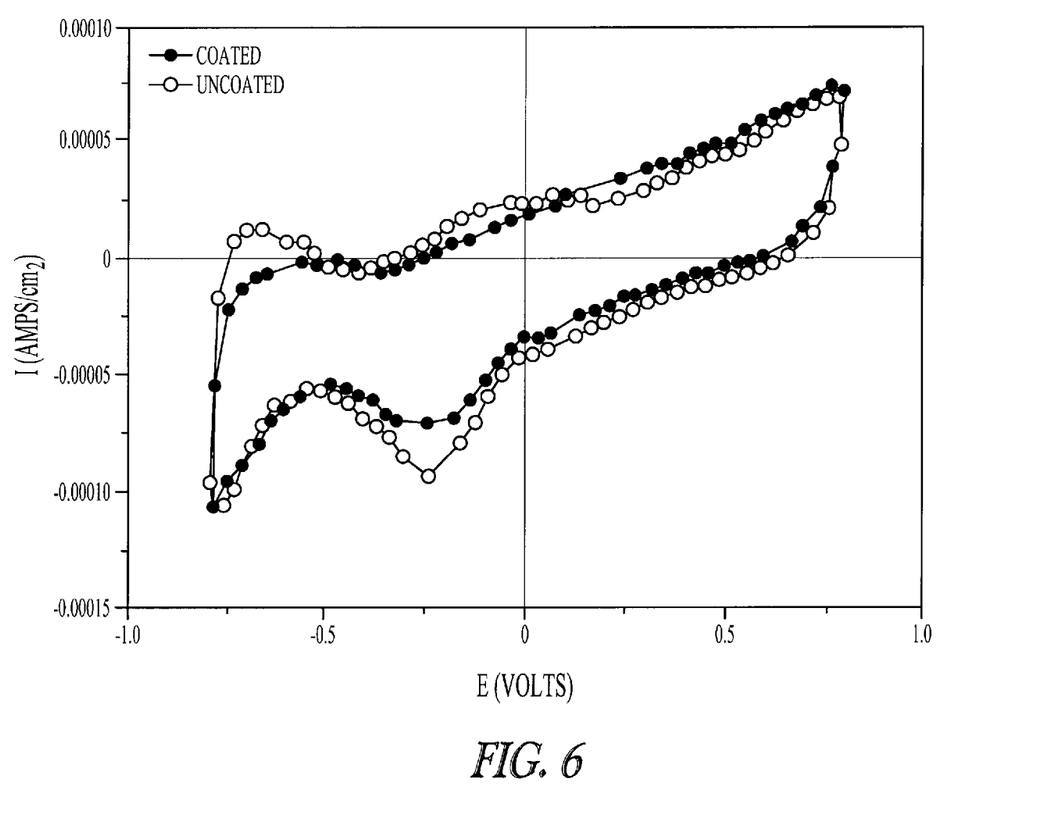
FIG. 6 is a graphical view of a cyclovoltammogram comparing a lead with a coating and a lead without the coating, according to some embodiments.
Figure 7:
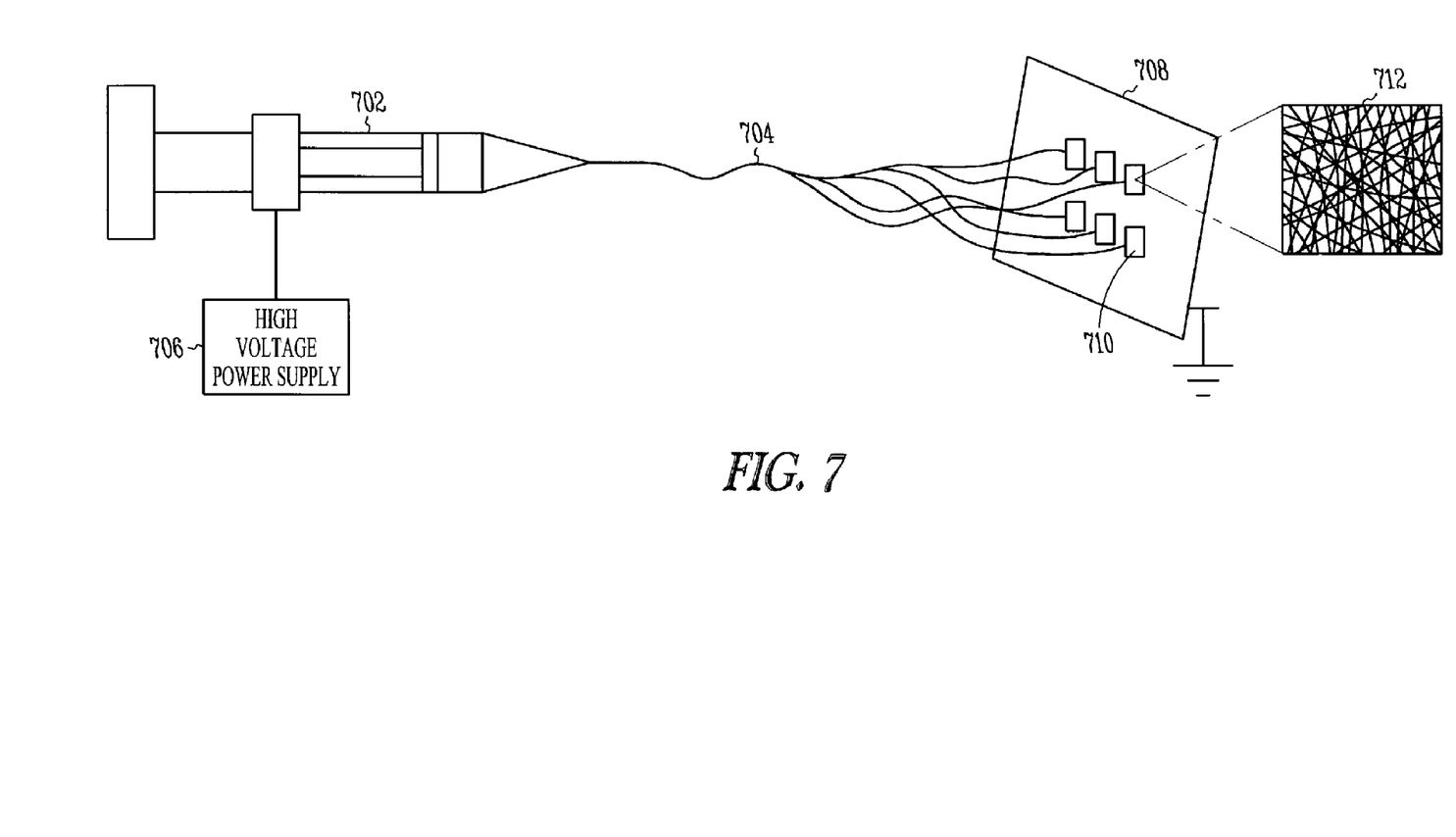
FIG. 7 is a perspective view illustrating the electrospinning of a fibrous matrix coating to a lead, according to some embodiments.

Referring to FIG. 5, a method of manufacturing a lead is shown, according to some embodiments of the invention. A lead may be formed 502. A fibrous matrix coating 310 may be disposed 504 on all or a portion of the lead 104. The coating 310 may be disposed by electrospinning, meltblowing or spinbonding, for example. Referring to FIG. 6, a graphical view is shown of a cyclovoltammogram displaying the similar electrical performance of a coated lead and an un-coated lead. In electrospinning, an electric field may be used to draw a polymer solution or melt 704 from a capillary source 702 as ultrafine jets, such as a syringe, to a grounded collector 708 (see FIG. 7). A high voltage power supply 706 may be used to power the process. The lead 104, or lead components 710, may be placed on the collector 708 to be coated. Upon drying, a thin polymeric web 712 may be formed with nanofibers having controllable diameters in the range of about 10-3000 nm, for example. The fiber diameter size may be about 40-2000 nm, about 50-1500 nm or about 100-1000 nm, for example. The fiber diameter size may be measured by taking the average or median size of the fibers or it may refer to the range of fiber sizes within a distribution. The size of the fibers can be controlled by adjusting the concentration of the solution introduced in the electrospinning process, for example. By disposing with meltblowing or spinbonding, the fiber size may be 1 to 2 orders of magnitude larger than when using electrospinning.

In order to substantially mimic the structure of tissue, the fibrous matrix coating 310 may comprise a three-dimensional structure. For example, the fibrous matrix coating 310 may have a fiber surface area per mass of fiber material in the range of about 0.1-100 $m^2/g$, about 0.2-2 $m^2/g$, about 2-20 $m^2/g$, about 20-80 $m^2/g$ or about 65-90 $m^2/g$ (based on fiber specific gravity of 1), for example. The basis weight range of the fibrous matrix coating 310 may be about 0.005-500 $g/m^2$, about 0.01-0.7 $g/m^2$, about 3-220 $g/m^2$ or about 8-350 $g/m^2$, for example. The fibrous matrix coating 310 may have pore sizes in the range of about 15 microns down to about 200 nm, or even less. The pore sizes may be about 0.01-15 microns, about 0.2-5 microns, about 100 nm-300 nm or less than about 200 nm, for example. The three-dimensional fibrous matrix coating 310 may have a porosity greater than about 40%, greater than about 60%, greater than about 75% or greater than about 85%, for example.

Examples of materials used to make a fibrous matrix coating 310 include natural and synthetic polymers. More specific examples include fibrin, elastin, fibronectin, Teflon®, carbon nanofibers, polypyrrole, polyethylenedioxythiophene, Nafion®, PEDOT, or combinations thereof. Examples of materials used to make a fibrous matrix coating 310 can also be found in commonly owned U.S. patent application Ser. No. 11/277,858, entitled "CONDUCTIVE POLYMERIC COATING WITH OPTIONAL BIOBENEFICIAL TOPCOAT FOR A MEDICAL LEAD," the disclosure of which is incorporated herein by reference in its entirety.

To allow for pacing/sensing/stimulation, the materials used to make a fibrous matrix coating 310 may be conductive, for example. Classes of conductive polymers include poly(acetylene)s, poly(pyrrole)s (PPy) (e.g., conductive polypyrrole polystyrene sulfonate), poly(thiophene)s (PT), poly(aniline)s, and poly(para-phenylene vinylene)s when combined with appropriate doping materials (e.g., doping materials are additives that facilitate the polymer conductivity). Conductive polymers also include silicone rubbers, polyurethane and homopolymers or copolymers of polyolefin, fluoropolymer, polyamide and polyester, combined with appropriate doping materials. Conductive polymers also include EHPT (poly(3-(2-ethylhexyl)thiophene), ionomers (e.g., Nafion®) and PEDOT (e.g., /PEDOT).

Nafion® is a member of a class of synthetic polymers with ionic properties which are called ionomers. (Nafion® is available commercially in several forms from, for example, Aldrich, including, but not limited to, Nafion® NR50, Nafion® perfluorinated resin solution, Nafion® perfluorinated resin, aqueous dispersion, Nafion® perfluorinated resin, powder, Nafion® SAC-13, and Nafion®, trimethylsilylated.) Nafion® is a perfluorinated polymer that contains sulfonic (sulfonated polytetrafluoroethylene polymer or perfluorocarbonsulfonic acid) or carboxylic ionic functional groups (e.g., a sulfonated tetrafluorethylene copolymer or a carboxylated tetrafluorethylene copolymer (polytetrafluorethylene)). In one embodiment, the perfluorinated polymer contains sulfonic functional groups. In another embodiment, the perfluorinated polymer contains carboxylic ionic functional groups.

PEDOT (also known as PEDT/ or PEDOT/) is the commercial name for a mixture of two components. One component in this mixture is made up of sodium polystyrene sulfonate which is a sulfonated polystyrene in which part of the sulfonyl groups are deprotonated. The other component, poly (3,4-ethylenedioxythiophene), is a conjugated polymer based on polythiophene. The chemical name of PEDOT: is poly(3,4-ethylenedioxythiophene) poly(styrenesulfonate).

In one embodiment, the conductive polymers are biocompatible (e.g., the polymers are not toxic or injurious to living tissue). Use of conductive polymers can reduce pacing threshold and improve sensing performance of the electrode along with improved biocompatibility of the electrode. For example, the use of conductive polymers on an electrode allows for the presentation of an organic interface to biological tissue instead of a metallic interface (e.g., a metallic electrode) for a favorable biological response to the implant. Inflammatory and healing response of the tissue can be controlled and altered to reduce myocyte necrosis in the area next to the lead and reduce thickness of fibrotic capsule.

In another embodiment of the invention, the materials used to make the fibrous matrix coating 310 are insulative, for example. By coating portions of a lead 104 with an insulative fibrous matrix coating, adhesion and tissue in-growth are promoted while simultaneously decreasing the surface area of one or more electrodes 208A, 208B, 208C, 208D creating a high impedance lead which decreases battery consumption of the IMD 102.

One embodiment of the fibrous matrix coating 310 provides a drug eluting lead or electrode which comprises at least one therapeutic agent. The drug or therapeutic agent may be chemically bound within the coating 310, such as within a copolymer, for example. The drug or therapeutic agent may be also physically/chemically adhere to or coat the fibers within the fibrous matrix coating 310, for example. Any drug or therapeutic agent may be chosen such that the subject's metabolism is capable of synthesizing it.

The therapeutic agent includes, but is not limited to an anti-inflammatory, anti-proliferative, anti-arrhythmic, anti-migratory, anti-neoplastic, antibiotic, anti-restenotic, anti-coagulation, anti-clotting (e.g., heparin, coumadin, aspirin), anti-thrombogenic or immunosuppressive agent, or an agent that promotes healing, such as a steroid (e.g., a glucocorticosteriod), and/or re-endothelialization or combinations thereof.

In essence, any drug or bioactive agent which can serve a useful therapeutic, prophylactic or even diagnostic function when released into a patient can be used. The agents may be used alone, in combinations of agents, admixed or chemically bound with the coating 310 or applied on top of, underneath or within the fibers of the coating 310.

More specifically, the therapeutic agents may include, but are not limited to paclitaxel, clobetasol, rapamycin (sirolimus), everolimus, tacrolimus, actinomycin-D, dexamethasone (e.g., dexamethasone sodium phosphate or dexamethasone sodium acetate), mometasone furoate, hyaluronic acid, vitamin E, mycophenolic acid, cyclosporins, beclomethasone (e.g., beclomethasone dipropionate anhydrous), their derivatives, analogs, salts or combinations thereof.

In one embodiment, a combination of an anti-proliferative (e.g., everolimus or paclitaxel) and an anti-inflammatory (e.g., dexamethasone, clobetasol or mometasone furoate) agent may be employed. In one embodiment, a combination of dexamethasone and everolimus is employed. In another embodiment, a combination of clobetasol and everolimus is employed. In yet another embodiment, a combination of dexamethasone and paclitaxel is employed. In another embodiment, a combination of clobetasol and paclitaxel is employed. In another embodiment, a combination of dexamethasone and sirolimus is employed. In one embodiment a combination of clobetasol and sirolimus is employed.

Additional suitable agents can be found in the Physicians Desk Reference (PDR) (see, for example, *The Physicians Desk Reference* (59th ed. 2005).

The therapeutic agent can be present in any effective amount. An "effective amount" generally means an amount which provides the desired local or systemic effect. For example, an effective dose is an amount sufficient to affect a beneficial or desired clinical result. The precise determination of what would be considered an effective dose may be based on factors individual to each patient, including their size and age. In one embodiment, the therapeutic agent is present in a concentration of less than about 100 µg/cm$^2$. For example, the agent may be present in a range of about 2 to about 10 µg/cm$^2$, about 10 to about 20 µg/cm$^2$, about 20 to about 30 µg/cm$^2$, about 30 to about 40 µg/cm$^2$, about 40 to about 50 µg/cm$^2$, about 50 to about 60 µg/cm$^2$, about 60 to about 70 µg/cm$^2$, about 70 to about 80 µg/cm$^2$, about 80 to about 90 µg/cm$^2$ and/or about 90 to about 100 µg/cm$^2$. The agent(s) may also be present at a concentration of higher than about 100 µg/cm$^2$.

In one embodiment, the agent eluting leads and/or electrodes can be delivered to a desired site within the patient's body. Once implanted, the therapeutic agent may elute from the surface of the implant and diffuse into the adjoining tissue. In this manner, the inflammatory process and/or other unwanted biological processes associated with implantation and the presence of the foreign object is suppressed (e.g., reduced inflammation and/or toxicity of inflammatory response). Additionally, the growth of non-excitable, connective tissue around the electrode (e.g., the capsule) is reduced (e.g., a reduction in fibrotic capsule thickness may be observed), and thus, the postoperative rise in the stimulation threshold lessens, a stable reduced threshold (when compared to the use of a lead without a coating as described here), both acute and chronic, is thereby provided. Additionally, the device and methods may prevent myocyte cell function impairment and/or necrosis around, near or on an electrode, which may further stabilize a reduced threshold.

In an embodiment, the therapeutic agent is available immediately after and/or during implantation (time of injury). In another embodiment, within a few days, such as about 1 to about 5 days, following implantation, the agent has nearly completely eluted. In another embodiment, the therapeutic agent elutes in a couple of hours to several days to several weeks (e.g., in about 1 to about 5 weeks). The therapeutic agent may also be designed to have longer eluting times, such as several months. Additionally, the lead may be designed so that one therapeutic agent is released at the time of implantation (time of injury), while another therapeutic agent releases more slowly, for example, over the course of about several weeks to about a month or two from the time of implantation. In one embodiment, the therapeutic agents may be the same or different therapeutic agents.

Embodiments of the invention provide a fibrous matrix coating disposed on all or a portion of a lead. The fibrous matrix coating may be conductive or insulative and may be comprised of differing materials depending on the position disposed on the lead. A single lead may comprise portions of the coating that encourage tissue in-growth for adhesion, such as near a pacing electrode, but also comprise a coating material that discourages tissue in-growth, such as on a defibrillating coil, for example. The fibrous matrix coating may comprise one or more drugs and encourage the biocompatibility of the lead with surrounding tissue, while also promoting healing and reduction of inflammation. The fibrous matrix coating mimics the three-dimensional structure of surrounding tissue which promotes adhesion and cell proliferation. The fibrous matrix coating may not require special storage procedures, may not contain contaminating biologics, may not require pH balancing and is reproducible in batches.

It is to be understood that the above description is intended to be illustrative, and not restrictive. It should be noted that the above text discusses and figure illustrate, among other things, implantable leads for use in cardiac situations; however, the present leads and methods are not so limited. Many other embodiments and contexts, such as for non-cardiac nerve and muscle situations or for external nerve and muscle situations, will be apparent to those of skill in the art upon reviewing the above description. The scope should, therefore, be determined with reference to the appended claims, along with the full scope of legal equivalents to which such claims are entitled.

What is claimed is:
1. A lead comprising:
a lead body extending from a lead proximal end portion to a lead distal end portion, and having an intermediate portion therebetween;
one or more tissue sensing/stimulation electrodes disposed along the lead body;
one or more terminal connections disposed along the lead proximal end portion;
one or more conductors contained within the lead body extending between the tissue sensing/stimulation electrodes and the terminal connections; and
a fibrous matrix coating substantially mimicking structure of tissue, disposed onto at least a portion of the lead body and/or sensing/stimulation electrodes;

wherein the fibrous matrix coating comprises fibers with diameters of about 10 nm to about 3000 nm and a basis weight of about 0.005 g/m² to about 500 g/m².

2. The lead of claim 1, further comprising one or more separators positioned between at least two electrodes.

3. The lead of claim 1, further comprising one or more drug collars positioned adjacent to the one or more electrodes.

4. The lead of claim 1, further comprising one or more modified surface layers, positioned above or below the fibrous matrix coating.

5. The lead of claim 4, wherein the one or more modified surface layers comprise layers modified by chemical etching, plasma etching, electrochemical etching or combinations thereof.

6. The lead of claim 4, wherein the one or more modified surface layers comprise layers of functional groups disposed by deposition, sputtering, coating, reactive ion etching, plasma polymerization or combinations thereof.

7. The lead of claim 1, wherein the fibrous matrix coating comprises a natural polymer, a synthetic polymer or combinations thereof.

8. The lead of claim 1, wherein the fibrous matrix coating comprises a conductive polymer, an insulative polymer or both.

9. The lead of claim 1, wherein the fibrous matrix coating is biocompatible.

10. The lead of claim 1, wherein the fibrous matrix coating comprises nanofibers.

11. The lead of claim 1, wherein the fibrous matrix coating comprises fibers with diameters of about 10-3000 nm.

12. The lead of claim 1, wherein the fibrous matrix coating comprises fibers with diameters of about 40-2000 nm.

13. The lead of claim 1, wherein the fibrous matrix coating includes one or more therapeutic agents or drugs.

14. The lead of claim 13, wherein the one or more therapeutic agents or drugs are chemically bound within the fibrous matrix coating.

15. The lead of claim 13, wherein the one or more therapeutic agents or drugs are coated on the fibers of the fibrous matrix coating.

16. A lead system comprising:
one or more leads, each lead comprising:
a lead body extending from a lead proximal end portion to a lead distal end portion, and having an intermediate portion therebetween;
one or more tissue sensing/stimulation electrodes disposed along the lead body;
one or more terminal connections disposed along the lead proximal end portion;
one or more conductors contained within the lead body extending between the tissue sensing/stimulation electrodes and the terminal connections;
a fibrous matrix coating substantially mimicking structure of tissue, disposed onto at least a portion of the lead body and/or sensing/stimulation electrodes;
wherein the fibrous matrix coating comprises fibers with diameters of about 10 nm to about 3000 nm and a basis weight of about 0.01 g/m² to about 500 g/m²;
a connector assembly, coupled to the one or more terminal connections; and
an implantable medical device, coupled to the connector assembly of the one or more leads.

17. The lead system of claim 16, further comprising an energy source coupled to the implantable medical device.

18. A method of manufacturing a lead, the method comprising:
forming a lead; and
disposing a fibrous matrix coating that substantially mimics structure of tissue, on all or a portion of the lead;
wherein the fibrous matrix coating comprises fibers with diameters of about 10 nm to about 3000 nm and a basis weight of about 0.01 g/m² to about 500 g/m².

19. The method of claim 18, further comprising after forming a lead, disposing a modified surface layer onto the lead.

20. The method of claim 18, further comprising after forming a lead, modifying the surface of the lead.

21. The method of claim 18, further comprising after disposing a matrix coating, disposing a modified surface layer onto the fibrous matrix coating.

22. The method of claim 18, wherein the disposing a fibrous matrix coating includes electrospinning.

* * * * *